(12) United States Patent
Burckhardt et al.

(10) Patent No.: US 10,772,669 B2
(45) Date of Patent: Sep. 15, 2020

(54) DRILL AND/OR GUIDE WIRE GUIDES FOR SURGICAL DRILL BITS, GUIDE WIRES AND/OR SCREWS AND METHODS OF USING SAID GUIDES

(71) Applicant: Flower Orthopedics Corporation, Horsham, PA (US)

(72) Inventors: Oliver Burckhardt, Philadelphia, PA (US); Brian Garvey, Media, PA (US)

(73) Assignee: FLOWER ORTHOPEDICS CORPORATION, Horsham, PA (US)

( * ) Notice: Subject to any disclaimer, the term of this patent is extended or adjusted under 35 U.S.C. 154(b) by 672 days.

(21) Appl. No.: 14/908,269

(22) PCT Filed: Jul. 31, 2014

(86) PCT No.: PCT/US2014/049204
§ 371 (c)(1),
(2) Date: Jan. 28, 2016

(87) PCT Pub. No.: WO2015/017681
PCT Pub. Date: Feb. 5, 2015

(65) Prior Publication Data
US 2016/0183995 A1  Jun. 30, 2016

Related U.S. Application Data

(60) Provisional application No. 61/861,483, filed on Aug. 2, 2013.

(51) Int. Cl.
*A61B 17/88* (2006.01)
*A61B 17/17* (2006.01)
(Continued)

(52) U.S. Cl.
CPC ...... *A61B 17/8897* (2013.01); *A61B 17/1728* (2013.01); *A61B 17/88* (2013.01); *A61B 2017/90* (2013.01); *A61B 2090/062* (2016.02)

(58) Field of Classification Search
CPC . A61B 17/1728; A61B 17/88; A61B 17/8897; A61B 2017/90
See application file for complete search history.

(56) References Cited

U.S. PATENT DOCUMENTS 3,704,707 A    12/1972  Halloran
4,570,624 A *  2/1986   Wu ..................... A61B 17/1728
                                                    606/96
(Continued)

FOREIGN PATENT DOCUMENTS

WO    WO2012080637 A1    6/2012

*Primary Examiner* — Anu Ramana
(74) *Attorney, Agent, or Firm* — Riverside Law LLP

(57) ABSTRACT

Drill and/or guide wire guides and methods are usable with at least one orthopedic surgical implant screw, wherein the guides have a length defined between a first end and a second end located opposite to the first end and a thickness defined between a front side and a back side located opposite to the front side of the guide. The guides have a guide hole formed adjacent to the first end of the guide, wherein the guide hole extends through the thickness of the guide from the front side to the back side of the guide, wherein the guide hole has a diameter sized to receive a diameter of a drill bit or a guide wire. The guides have a slot formed on the front side of the guide and located adjacent to the front side of the guide, wherein the slot extends along at least a portion of the length of the guide, wherein the slot has a diameter sized to receive a diameter of a drill bit or a guide wire. The longitudinal axis of the guide hole is angled from a longitudinal axis of the guide or the slot by an angle a, wherein the angle a is greater than about 1° and less than about 90°.

21 Claims, 6 Drawing Sheets

(51) Int. Cl.
 *A61B 17/90* (2006.01)
 *A61B 90/00* (2016.01)

(56) References Cited

U.S. PATENT DOCUMENTS

| | | | |
|---|---|---|---|
| 5,180,388 A * | 1/1993 | DiCarlo | A61B 17/17 606/102 |
| 2007/0083210 A1 | 4/2007 | Hestad et al. | |
| 2010/0145340 A1 | 6/2010 | Phan et al. | |
| 2011/0190825 A1 * | 8/2011 | Thalgott | A61B 17/70 606/279 |
| 2012/0239044 A1 | 9/2012 | Kam et al. | |
| 2013/0012945 A1 | 1/2013 | Chreene et al. | |
| 2013/0267836 A1 * | 10/2013 | Mauldin | A61B 6/12 600/424 |

* cited by examiner

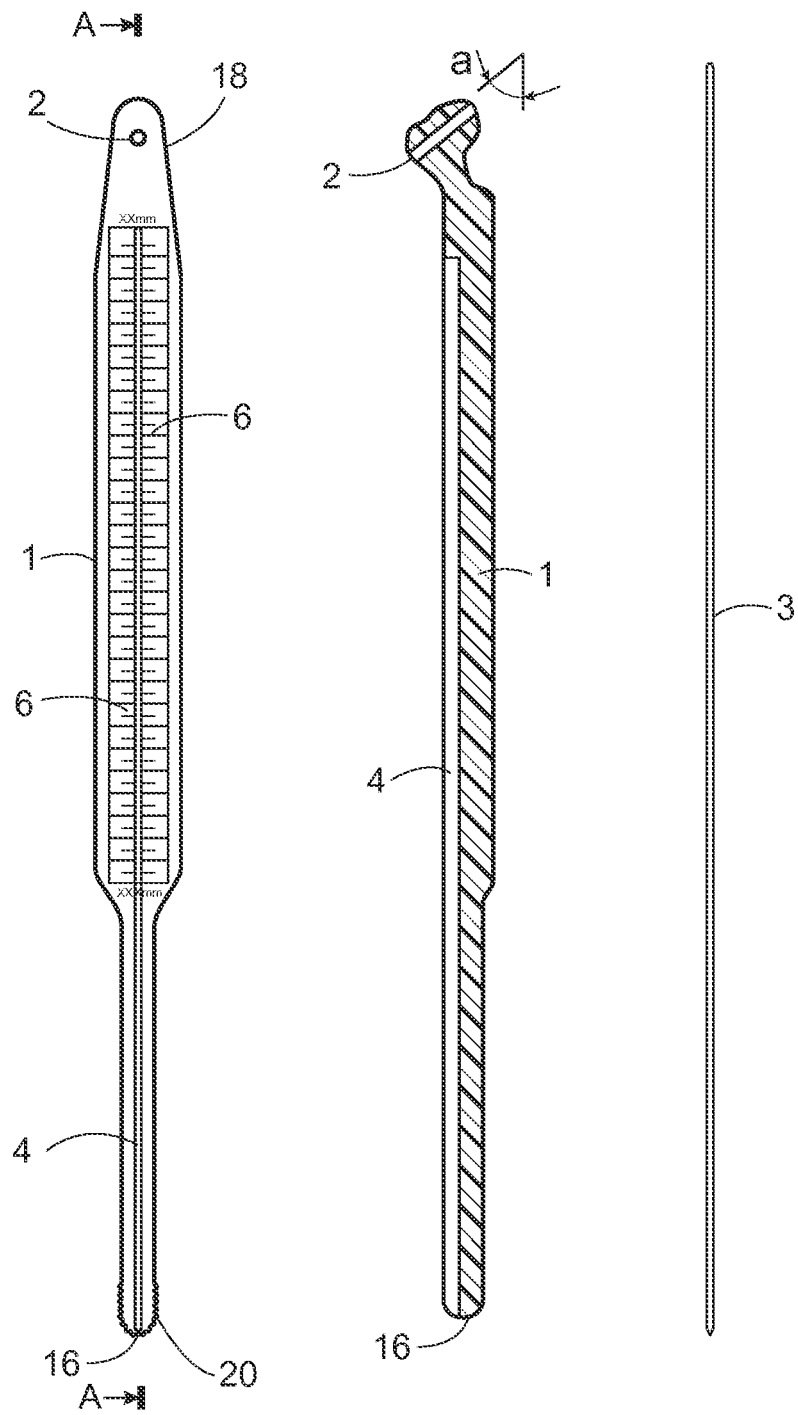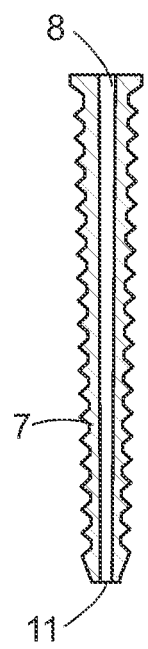

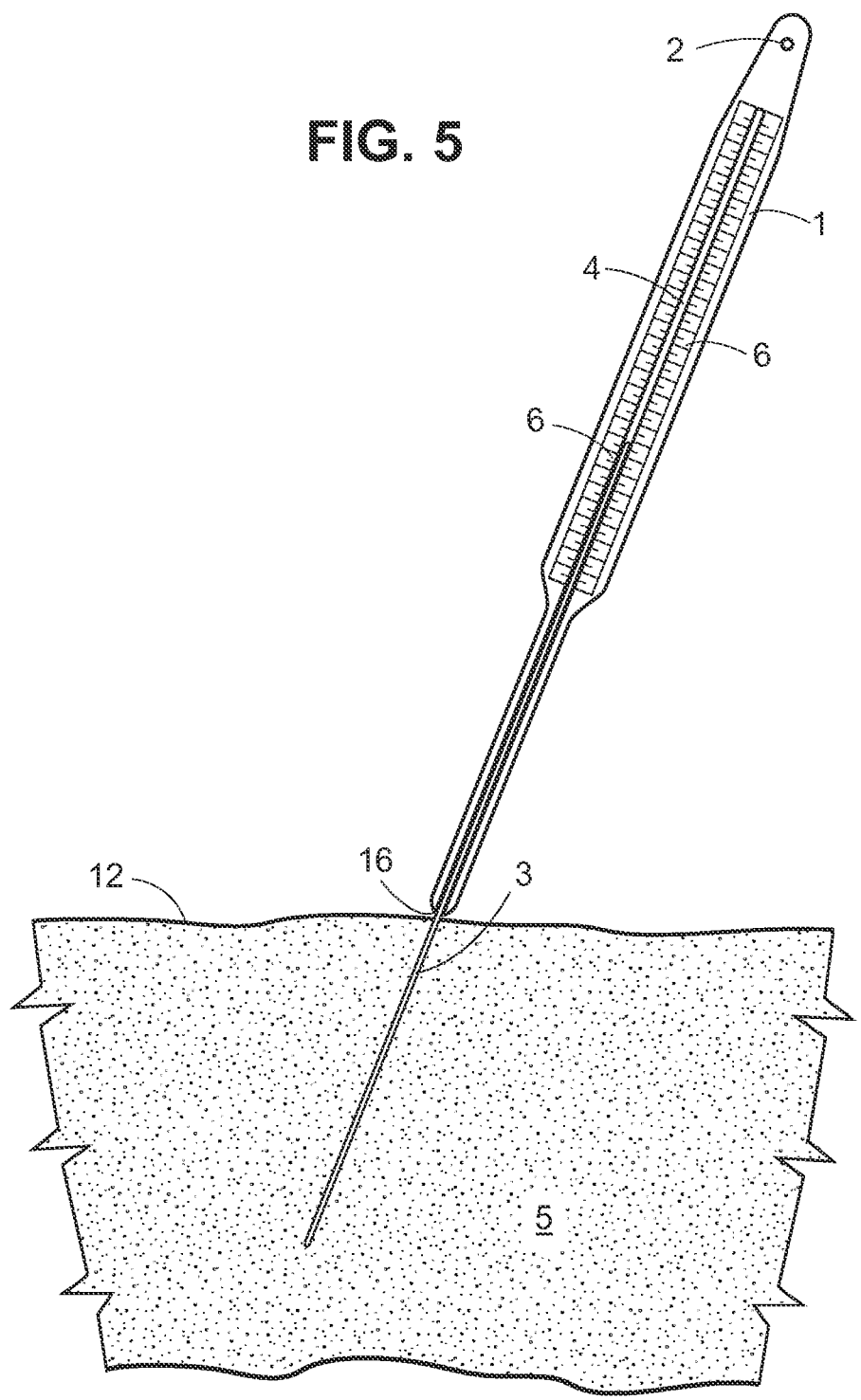

DRILL AND/OR GUIDE WIRE GUIDES FOR SURGICAL DRILL BITS, GUIDE WIRES AND/OR SCREWS AND METHODS OF USING SAID GUIDES

This application is the U.S. national phase application filed under 35 U.S.C. § 371 claiming benefit to International Patent Application No. PCT/US2014/49204, filed Jul. 31, 2014, which is entitled to priority under 35 U.S.C. § 119(e) to U.S. Provisional Patent Application No. 61/861,483, filed Aug. 2, 2013, each of which applications are incorporated by reference herein in their entireties.

FIELD OF THE DISCLOSURE

The present disclosure relates to drill and/or guide wire guides for surgical implant drill bits, guide wires and/or cannulated screws and methods of using said guides. Each of the drill and/or guide wire guides, drill bits, guide wires and/or cannulated screws are sterile, contained in one or more individual sterile packages, and/or immediately ready for surgery upon removal from the packages without pre-operation processing. The drill and/or guide wire guides, drill bits, guide wires are disposable and may be disposed of after being used during a surgical procedure without post-operation reprocessing. The drill and/or guide wire guides may be utilized during the surgical procedure to drill, insert, twist and/or screw at least one drill bit and/or guide wire into a bone.

In a surgical procedure to repair a broken bone, or fuse two or more bones of a joint, using a bone plate implant, at least one screw is traditionally used to affix the bone plate implant to the bone, and/or at least one screw is traditionally used to fix the fragments or bones to each other. The present drill and/or guide wire guides may assure, confirm and/or make certain that a desired, required, proper and/or necessary trajectory (hereinafter "desired trajectory") of the drill bit, guide wire and/or at least one screw into the bone is produced, followed and/or achieved when the drill bit and/or guide wire twists, screws, drills or pushes into the bone and/or when the at least one screw is screwed into the bone. Further, the present drill and/or guide wire guides may insure that the proper screw length is used to affix the bone plate implant to the bone, and/or insure that the proper length screw is used to fix the fragments or bones together, i.e. using a screw without a bone plate.

It is well known to use drill guides to pre-drill a hole into the bone at a proper trajectory to be followed by a screw. In some cases, however, the screw may not follow the hole when it is screwed into the bone. And when self-tapping screws are used, it is more difficult to control the trajectory because there is no pre-drilled hole for the screw to follow. The present guide wires for cannulated screws assure, confirm and/or make certain that the screw follows the desired trajectory into the bone. The present drill and/or guide wire guides may also provide a measuring device for determining, identifying and/or measuring a depth of the guide wire into the bone and/or a depth of a pre-drilled hole into the bone. As a result of measuring the depth of the guide wire and/or pre-drilled hole, a proper screw length for affixing the bone plant implant to the bone may be determined, selected, identified and/or utilized. Each guide wire may be a stiff, rigid metal wire or steel wire that is configured and/or adapted to be drilled, screwed, inserted and/or twisted into a bone without a pre-drilled hole in case a self-tapping screw may be used during the surgical procedure to affix the bone plate implant to the bone and/or inserting a screw into a bone without a bone plate. Each guide wire may be made of a metallic material that is strong enough to penetrate the surface of the bone and/or the interior of the bone.

SUMMARY OF THE DISCLOSURE

In an embodiment, a drill or guide wire guide for use with at least one surgical implant screw may have a length defined between a first end and a second end located opposite to the first end and a thickness defined between a front side and a back side located opposite to the front side of the guide. The guide may have a guide hole formed adjacent to the first end of the guide, wherein the guide hole extends through the thickness of the guide from the front side to the back side of the guide, wherein the guide hole has a diameter sized to receive a diameter of a drill bit or a guide wire. Further, the guide may have a slot and/or cannula formed on the front side of the guide and located adjacent to the second end of the guide, wherein the slot and/or cannula extends along at least a portion of the length of the guide, wherein the slot has a diameter sized to receive a diameter of a drill bit or a guide wire, wherein, when the cannula is provided, the cannula may extend along the entire length of the slot or less than the entire length of the slot. A longitudinal axis of the guide hole may be angled from a longitudinal axis of the guide or the slot by an angle a, wherein the angle a is greater than about 1° and less than about 90°.

In an embodiment, the angle a may be greater than about 30° and less than about 60°.

In an embodiment, the angle may be is greater than about 45° and less than about 50°.

In an embodiment, an entire length of the slot and/or cannula may be positioned between the guide hole and the second end of the guide.

In an embodiment, the guide may have one or more sharp edges provided on at least one of the first end and second end of the guide, wherein the one or more sharp edges are configured to countersink a bone when the one or more sharp edges are positioned directly against the bone and rotated or moved.

In an embodiment, the one or more sharp edges may comprise at least one of serrations and flutes.

In an embodiment, a cross-sectional shape of the one or more sharp edges may be at least one of a circular shape and a semi-circular shape.

In an embodiment, the slot and/or cannula may extend over more than about 30% of the length of the guide.

In an embodiment, the guide may be provided with a guide wire having a pre-determined length and a diameter less than the diameters of the guide hole and the slot such that the guide wire is insertable into the guide hole or the slot.

In an embodiment, the guide may have a measuring scale positioned adjacent to the slot for measuring an exposed portion of a length of a guide wire when the guide wire is positioned within the slot.

In an embodiment, at least a portion of the slot and/or cannula may extend through an entire length of the measuring scale.

In an embodiment, the measure scale may range from at least about 5 mm to no more than about 250 mm.

In embodiments, a method may guide a cannulated screw along a desired trajectory in a bone in orthopedic surgery. The method may provide the guide in an individual sterile package, insert a guide wire into a bone at the desired trajectory via the guide hole of the guide, insert the guide wire into a shaft of a surgical implant screw such that a first end of the screw is contactable with an outer surface of the bone, and/or insert the screw into the bone along the desired trajectory provided by the guide hole of the guide.

In an embodiment, the method may remove the guide wire when the trajectory of the surgical implant screw has been established, wherein the surgical implant screw is a cannulated screw.

In an embodiment, the method may countersink the bone by rotating or moving one or more sharp edges of the guide against the bone to remove a portion of the bone, wherein the one or more sharp edges are positioned on at least one of the first end and second end of the guide.

In an embodiment, the one or more sharp edges may comprise at least one of serrations and flutes, wherein, when the one or more sharp edges comprise at least flutes, the flutes may be curved flutes.

In embodiments, a method may select a screw having a desired length. The method may provide the guide in an individual sterile package, partially insert a portion of a guide wire having a pre-determined length into a bone, measure a portion of the guide wire that has not been inserted into the bone via the slot provided on the front side of the guide, determine a depth of the guide wire inserted into the bone based on the measured portion of the guide wire, and/or determine the desired length of the screw by adding the determined depth of the guide wire inserted into the bone and a distance that is traversable by the screw in a bone plate implant, when a bone plate implant is to be affixed to the bone.

In an embodiment, the screw may be a cannulated screw.

In an embodiment, the portion of the guide wire that has not been inserted into the bone may be inserted into the slot of the guide to determine the measured portion of the guide wire.

In an embodiment, a measuring scale may be located adjacent to the slot for determining the measured portion of the guide wire.

BRIEF DESCRIPTION OF THE DRAWINGS

So that the features and advantages of the present disclosure can be understood in detail, a more particular description of the guides and methods may be had by reference to the embodiments thereof that are illustrated in the appended drawings. It is to be noted, however, that the appended drawings illustrate only some typical embodiments of the present guides and methods and are therefore not to be considered limiting of its scope, for the guides and methods may admit to other equally effective embodiments.

FIG. 1 illustrates a front plan view of a drill and/or guide wire guide having a wire depth measuring device in an embodiment.

FIG. 2 illustrates a cross-sectional view of the drill and/or guide wire guide shown in FIG. 1 taken along section line A-A of FIG. 1 in an embodiment.

FIG. 3 illustrates a front plan view of a guide wire in an embodiment.

FIG. 4 illustrates a cross-sectional view of a cannulated screw in an embodiment.

FIG. 5 illustrates the drill and/or guide wire guide shown in FIG.1 being utilized to insert the guide wire shown in FIG. 3 in a bone in an embodiment.

DETAILED DESCRIPTION OF THE DISCLOSURE

Figure 6A:
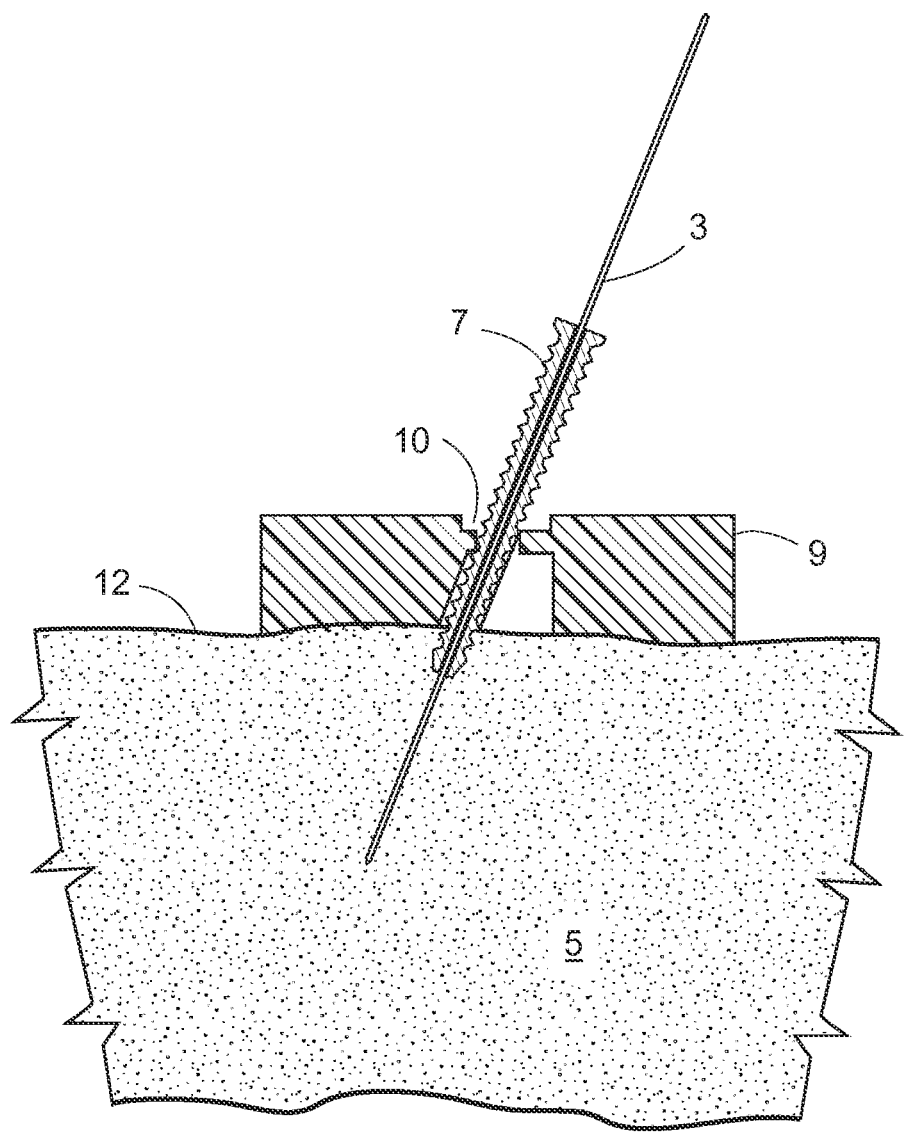
FIG. 6A illustrates the guide wire of FIG. 5 guiding a self-tapping cannulated screw through a bone plate and into the bone shown in FIG. 5 in an embodiment.

Referring now to the drawings wherein like numerals refer to like parts, FIG. 1 shows a drill and/or guide wire guide 1 (hereinafter "guide 1"), and FIG. 2 shows a cross-sectional view of guide 1 along section line A-A of FIG. 1. The guide 1 has a length defined between a distal end 16 and a proximal end 18 and a thickness defined between a front side and a back side located opposite to the front side. A guide hole 2 (hereinafter "hole 2") is provided at the proximal end 18 of guide 1 and extends through the thickness of the guide 1 from the front side of the guide 1 to the back side of the guide 1 as shown in FIG. 2. The hole 2, formed through the thickness of the guide 1, may be sized, shaped, configured and/or adapted for guiding, pointing and/or extending a guide wire 3, illustrated in FIG. 3, and/or a drill bit 13, illustrated in FIG. 7, at the desired trajectory necessary for completing the surgical procedure.

A slot or cannula 4 (hereinafter "slot 4") may be provided adjacent to the distal end 16 of the guide 1. The slot 4 is formed on the front side of the guide 1 and/or may extend away from the distal end and along at least a portion of the length of guide 1, or along a majority of the length of guide 1. The majority of the length of the guide 1 may be at least about 50% of the length, at least about 75% of the length, at least about 85% of the length or at least about 90% of the length of guide 1. The slot 4 may be sized, shaped, configured and/or adapted to receive the guide wire 3 after the guide wire 3 may have been inserted into a bone 5 as illustrated in FIG. 5. The guide 1 may provide a depth measuring device, such as, for example, a scale 6 that is provided and/or formed on the front side of the guide 1 alongside slot 4 to determine, identify and/or measure a depth of the guide wire 3 and/or the drill bit 13 in the bone 5 or a depth of a pre-drilled hole in the bone 5. The depth may be determined, indentified and/or measured, via the slot 4 and/or scale 6, based upon the known length of guide wire 3 and/or drill bit 13 as will be apparent to those having ordinary skill in the art. In embodiments, the scale 6 may be located on both side of and/or may surround the slot 4. In embodiments, one or more portions of the slot 4 may extend through one or more portions of the scale 6. In an embodiment, the diameter of the hole 2 and/or the diameter of the slot 4 may be continuous along a portion of the length, or along the entire length, of the hole 2 and/or slot 4, respectively.

Figure 7:
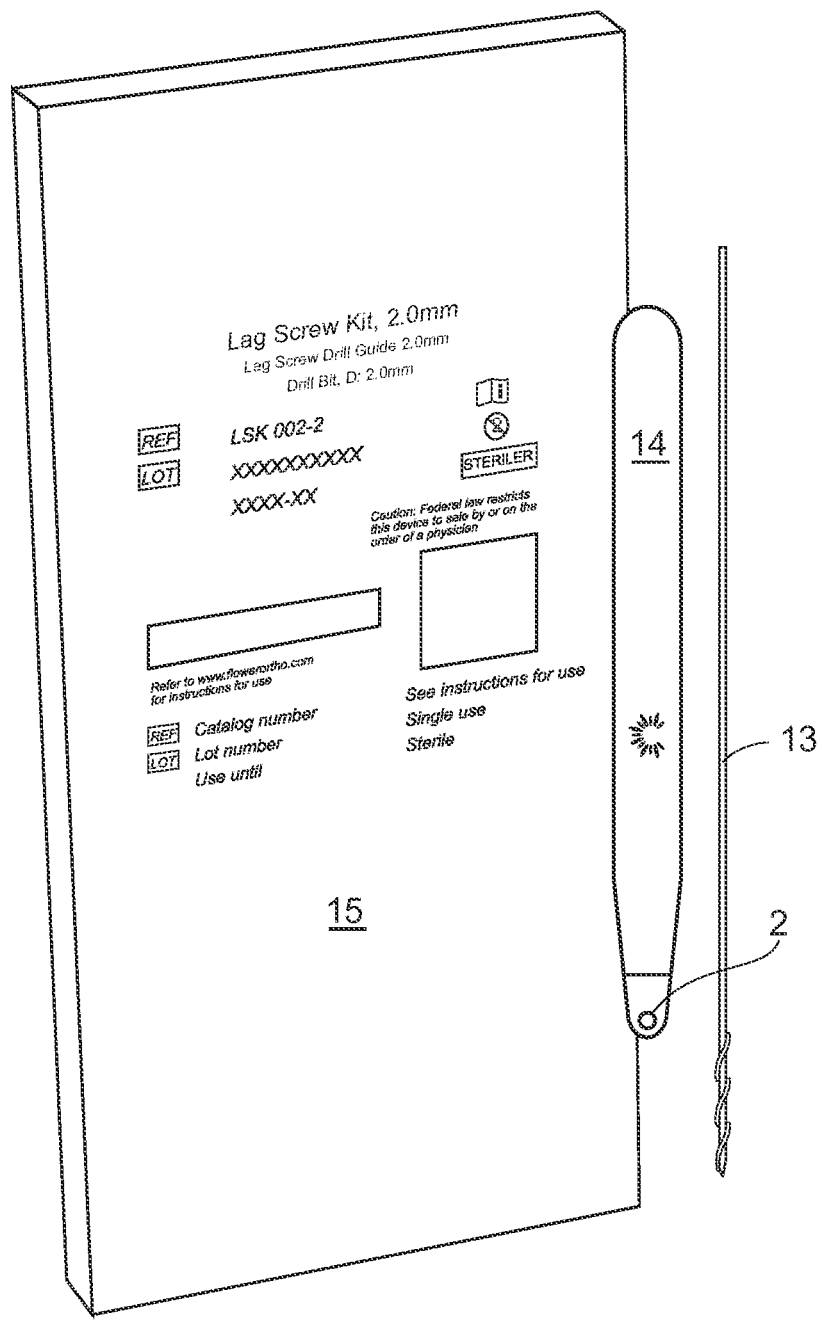
FIG. 7 illustrates a perspective view of an individual sterile package with sterile contents of the package outside of and alongside of the package in an embodiment.

FIG. 4 shows a surgical screw 7 (hereinafter "screw 7") for affixing a bone plate implant 9 (hereinafter "implant 9"), shown in FIG. 6A to the bone 5, and FIG. 7 shows a drill bit 13 and drill and/or guide wire guide 14 (hereinafter "guide 14") which is provided in an individual sterile package 15 for drilling and/or forming a hole in the bone 5. One or more of the guide 1, guide wire 3, the screw 7, the implant 9, the drill bit 13 and/or the guide 14 may be delivered to an operating room or suite to be utilized during and/or to complete a surgical operation or procedure, such as, for example, a bone plate fixation procedure, an internal fixation procedure and/or a bone plating or implantation procedure (hereinafter "surgical procedure"). In embodiments, the drill bit 13 and guide 14 may be utilized to provide or drill a pre-drilled hole into the bone 5.

In embodiments, the screw 7 may be a sterile locking screw (not shown in the drawings), a sterile non-locking screw (not shown in the drawings) or a cannulated screw as shown in FIG. 4, and the screw 7 may be fully-threaded or at least partially threaded. In embodiments, the guide 14 may have the same or substantially the same structure features as the guide 1, namely, the guide 14 may have the hole 2 at a proximal end 18 of the guide 14 and the slot 4 and/or the scale 6 located adjacent a distal end 16 of the guide 14. In an embodiment, the guide 14 may have the hole 2 but the slot 4 and scale 6 may be excluded from the guide 14 as shown in FIG. 7.

Each of the guide 1, guide wire 3, the screw 7, the implant 9, the drill bit 13 and/or the guide 14 are sterile and are provided one or more, or a plurality of, individual sterile packages which are contained within a single-use, sterile orthopaedic implant kit (not shown in the drawings). In embodiments, the implant kit may be refilled by a provider or a re-filling third party after the contents of one or more of the individual sterile packages of the implant kit have been removed from the implant kit to be utilized during the surgical procedure. Each of the guide 1, the guide wire 3, the screw 7, the implant 9, the drill bit 13 and/or the guide 14 are ready for surgery after being removed from individual sterile packages without any pre-operating processing. One or more of the guide 1, the guide wire 3, the drill bit 13 and/or the guide 14 are disposable and may be disposed of after being utilized during the surgical procedure without post-operating processing. The guide 1, guide wire 3, the screw 7, the implant 9, the drill bit 13, the guide 14 and/or the implant kit may (i) provide guaranteed sterility, (ii) require no pre-or post-operating processing, (iii) eliminate reprocessing cost, (iv) limit risk of infection and/or (v) expedite operating room turnaround.

The guide 1, the guide wire 3, the screw 7, the implant 9, the drill bit 13, the guide 14 and/or the implant kit may be used for internal fixation of fractures and/or reconstruction of one or more bones. The one or more bones may include every bone in the human or vertebrate body, such as, for example, scapula, olecranon, humerus, radius, ulna, pelvis, tibia, fibula, clavicle, vertebrae, femur, cranium, hand bones and/or foot bones. The internal fixation and/or reconstruction may include compression fractures, intra-articular and/or extra-articular factures, displaced fractures, osteotomies, non-unions and/or mal-unions. Moreover, the guide 1, guide wire 3, the screw 7, the implant 9, the drill bit 13, the guide 14 and/or the implant kit are may be used for palmar, ventral, dorsal and/or orthogonal applications. It should be understood that the present disclosure is not limited to a specific embodiment of the bones, the internal fixation, reconstruction and/or application.

In embodiments, the guide 14, a pair of the guide wire 3 and/or a cannulated screwdriver (not shown in the drawings) may be provided in an individual sterile guide wire packaged kit which may contain necessary instruments required for placing, positioning and/or inserting at least one guide wire 3 and/or the screw 7 into the bone 5. Each guide wire 3 may have a threaded tip that may stabilize and/or maintain the alignment and/or positioning of the guide wire 3 during drilling, screwing, twisting and/or inserting the guide wire 3 and/or the screw 7 into the bone 5. The guide 14, having the hole 2, and optionally the slot 4 and/or the scale 6, allows for drilling into the bone to a desired depth and measuring the desired depth to identify and/or determine the proper screw length for the screw 7. The screwdriver may slide over the guide wire, having been inserted into the bone 5, for enabling or providing guided placement for the screw 7. Each guide wire 3 may have a diameter in the range of about 0.5 to about 1.5 mm, or from about 0.8 to about 1.1 mm. The hole 2 and/or the slot 4 may have a diameter in a range that corresponds or substantially corresponds to the diameter range of each guide wire 3. As a result, the guide wire 3 may be inserted into the hole 2 and/or the slot 4, and the hole 2 and/or the slot 4 may receive, hold and/or grip the guide wire 3 therein during the surgical procedure.

The screw 7 may have a diameter in the range of about 0.5 to about 5.5 mm, about 2.0 to about 4.5 mm, about 2.4 to about 4 mm or about 3 to about 3.5 mm. The screw 7 may have a length in a range of about 5 to about 50 mm, about 10 to about 40 mm or about 20 to about 30 mm. In embodiments, the screw 7 may be accompanied by sterile countersinks (not shown in the drawings) and/or sterile screw washers (not shown in the drawings). In embodiments, the sterile countersinks may have a diameter in the range of about 1.0 to about 5.5 mm, and the screw washers may have a diameter in the range of about 2.0 to about 5.5 mm.

In embodiments, the drill bit 13 and the guide 14 may be provided in an individual sterile drill bit packaged kit or an individual sterile lag screw packaged kit. The drill bit packaged kit may contain instruments necessary for preparing a pilot hole for the screw 7, when the screw 7 is a locking screw or a non-locking screw, to secure the implant 9 to the bone 5. The lag screw packaged kit may contain necessary instruments for applying fracture compression when performing a lag screw technique through the implant 9. The drill bit 13 may have a diameter that matches or corresponds to the diameter of screw 7 and/or the hole 2, and may provide oversized drilling when the screw 7 is a lag screw (not shown in the drawings). For example, the drill bit 13 and/or the hole 2 may have a diameter in the range of about 0.5 to about 4.0 mm, about 1.1 to about 3.0 mm, about 1.5 to about 2.5 mm or about 1.8 to about 2.0 mm.

The guide 1 and/or guide 14 (hereinafter collectively referred to as "guides 1, 14") may be positioned or provided at a screw hole position such that the guides 1, 14 may provide soft tissue protection and/or the desired trajectory for placement of the guide wire 3 and/or the screw 7 with respect to the bone 5. If compression is desired during the surgical procedure, an off-center hole may be drilled through an end of one of the guides 1, 14, which may allow bone compression during insertion of the screw 7 into the bone 5. The slot 4 of the drill guides 1, 14 may have a diameter in the range of about 0.5 to about 5.0 mm, about 1.5 to about 4.0 mm, about 2.0 to about 3.5 mm or about 2.4 to about 3.5 mm.

For the guides 1, 14, the longitudinal axis of the hole 2 is angled or separated, by an angle a, from the longitudinal axis of the guides 1, 14 and/or of the slot 4. The angle a may be an angle of about 1 to about 90 degrees, about 30 to about 60 degrees, about 40 to about 50 degrees, about 43 to about 47 degrees or about 45 degrees. In embodiments, the scale 6 of the guides 1, 14 may have values ranging from about 1 to 200 mm, about 5 to about 150 mm, about 10 to about 130 mm or about 20 to about 110 mm. When the guides 1, 14 are positioned in an upright position as shown in FIGS. 1 and 5, the largest value (i.e., 150 mm) of the scale 6 is located at the bottom end of the scale 6 adjacent to the distal end 16 of the guides 1, 14, and the smallest value (i.e., 10 mm) is located at the top end of the scale adjacent to the proximal end 18 of the guides 1, 14.

Figure 8:
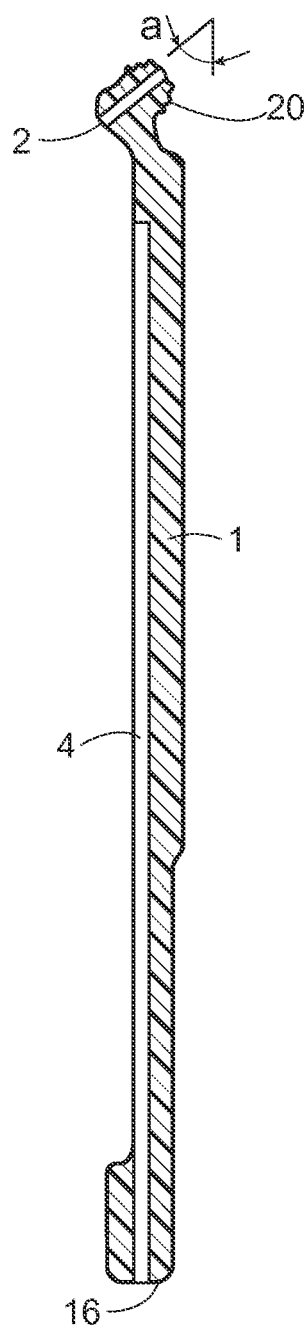
FIG. 8 illustrates a cross-sectional view of a drill and/or guide wire guide having holes provided at both ends of the guide in an embodiment.

In embodiments the guides 1, 14 may have one or more sharp edges 20 (hereinafter "edges 20") configured to cut or scrap away one or more portions of the bone 5 during the surgical procedure and/or prior to insertion of the screw 7 into the bone. The edges 20 may be positioned and/or provided on at least one of the distal end 16 and the proximal end 18 of the guides 1, 14 as shown in FIGS. 1 and 8. The edges 20 may be a sharp scraping and/or cutting edge to cut, scrap and/or remove portions of the bone 5. For example, the edges 20 may be at least one of one or more serrations or a plurality of cutting flutes 24 on a surface 22 of the distal end 16 and/or the proximal end 18 as shown in FIG. 9.

The edges 20 of the guides 1, 14 may be positioned and/or located in direct contact with a portion of the bone which is to cut or scraped away or to be removed before and/or during the surgical procedure to provide countersinking of the bone 5. Once in contact with the portion of the bone 5, the edges 20 and/or the guides 1, 14 may be rotated, turned, twisted and/or moved back and forth against the portion of the bone 5. As a result, the portion of the bone may be cut or scraped away or removed from the bone 5 to produce a countersink (not shown in the drawings) for the head of the screw 7 in the bone 5. The countersink may be produced by the edges 20 of the proximal end 18 when the proximal end 18 is in direct contact with the bone 5 and/or by the edges of the distal end 16 when the distal end 16 is in direct contact with the bone 5. Thus, at least one the ends 16, 18 of the guides 1, 14 may be utilized to form, produce or provide the countersink for the head of the screw 7 in the bone 5.

Figure 9:
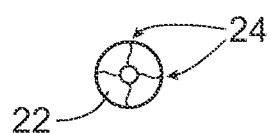
FIG. 9 illustrates a tip or surface of an end of the drill and/or guide wire guide shown in FIG. 8 in an embodiment.

In embodiments, the distal end 16 of the guides 1, 14 may provide with a hole extending therethrough as shown in FIGS. 8 and 9. One or more portions of the distal end 16 may extend entirely around the slot 4 adjacent to the distal end 16 to provide the hole. Dimensions and/or diameter of the hole are the same as or substantially similar to the dimensions and/or diameter of the slot 4 and/or hole 2. The hole at the distal end of the guides 1, 14 may be sized, shaped, configured and/or adapted to receive, house and/or enclose the diameter of guide wire 3 and/or the drill bit 13. As a result, the hole at the distal end of the guides 1, 14 may be utilized to guide and/or measure the guide wire 3 and/or the drill bit 13 during the surgical procedure.

In embodiments, a tip or surface 22 (hereinafter "surface 22") may be provided at the distal end 16 and/or proximal end 18 and may be a flat surface, a curved surface and/or a rounded surface. The edges 20 may be provided on the surface 22 for removing one or more portions of the bone 15 to produce the countersink in the bone 5. In embodiments, a plurality of the cutting flutes 24 may be provided on the surface 22 for removing one or more portions of the bone 15 to produce the countersink in the bone 5 as shown in FIG. 9. In an embodiment, the edges 20 and/or the cutting flutes 24 may have a curved cross-sectional shape, a circular cross-sectional shape and/or a semi-circular cross-section shape. In embodiment, the edges 20 and/or the cutting flutes 24 may be made of a hard, rigid material that is strong enough to cut or scrap away or remove the portion of the bone 5, by rotating, turning, twisting and/or moving the guides 1, 14 back and forth, to produce the countersink in the bone 5.

During the surgical procedure, one of the guides 1, 14, which is sterile, may be removed from the individual sterile package by a user. The user may position a first end of the hole 2, that is located opposite the slot 4 as shown in FIG. 2, adjacent to, against, next to and/or besides the portion of the bone 5 that is to receive the guide wire 3, the drill bit 13 and/or the screw 7. As a result of the angle a of the hole 2, the desired trajectory for the guide wire 3, the drill bit 13 and/or the screw 7 may extend outwardly away from the end of the hole 2 adjacent to the bone 5 and/or into the portion of the bone 5. When the guide wire 3 or the drill bit 13 are being used. The guide wire 3 or the drill bit 13 is inserted into a second end of the hole 2 that is opposite to the first end of the hole 2 and the bone 5. The guide wire 3 or the drill bit 13 may be drilled, screwed, twisted, turned and/or inserted into the bone 5 at the desired trajectory via the first end of the hole 2 and/or the angle a of the hole 2. As a result, the guide wire 3 or the drill bit 13 is drilled, screwed, twisted, turned and/or inserted into the bone 5 at the desired trajectory and at a measurable depth.

An exposed or non-inserted portion of the guide wire 3 or the drill bit 13 may be placed in the slot 4 as the distal end 16 of one of the guides 1, 14 may be placed on the surface 12 of bone 5 as shown in FIG. 5. The scale 6, provided alongside the slot 4, may measure, identify and/or determine the depth of the guide wire 3 or the drill bit 13 in the bone 5 based upon the exposed or non-inserted portion of the guide wire 3 or the drill bit 13 and/or the known length of guide wire 3 or the drill bit 13 as will be apparent to those having ordinary skill in the art. As a result, the desired screw length for screw 7 may then be determined, identified, calculated and/or measured based upon the measured depth of the guide wire 3 or the drill bit 13. In embodiments when the implant 9 is to be used in the surgical procedure, the desired screw length for screw 7 may then be determined, identified, calculated and/or measured based upon the measured depth of the guide wire 3 or the drill bit 13 and/or the thickness of the implant 9 at the section of the implant 9 that will be traversed by the screw 7. In embodiments, the angle a of hole 2 which corresponds to and/or is indicative of the desired trajectory may be taken into account, considered and/or utilized to determine, identify, calculate and/or measure the desired screw length of the screw 7 that will be traversing the implant 9.

For example, the guide wire 3 may have a pre-determined length, such as, 160 mm. When the guide wire 3 is positioned within or moved into the slot 4 of one of the guides 1, 14, the end of the guide wire 3, or exposed portion of the guide wire 3, located in the slot 4 aligns with or is adjacent to a value of 130 mm on scale 6. Therefore, it is determined that 30 mm of the guide wire 3 is inserted into the bone 5 based on the value of 130 mm of the scale 6. Therefore, the desired screw length for screw 7 is determined or calculated to be 30 mm.

The screw 7, illustrated in FIG. 4, has a shaft 8 through the center of the screw 7 which may extend along the entire length of the screw 7 from a first end to a second end of the screw 7. In embodiments, the shaft 8 may have a diameter that may be continuous along the entire length of the screw 7 from the first end to the second end of the screw. The diameter of the shaft 8 may be substantially the same as and/or greater than the diameter of the guide wire 3. As a result, the guide wire 3 may be inserted, positioned and/or moved into the shaft 8 of the screw 7.

Figure 6B:
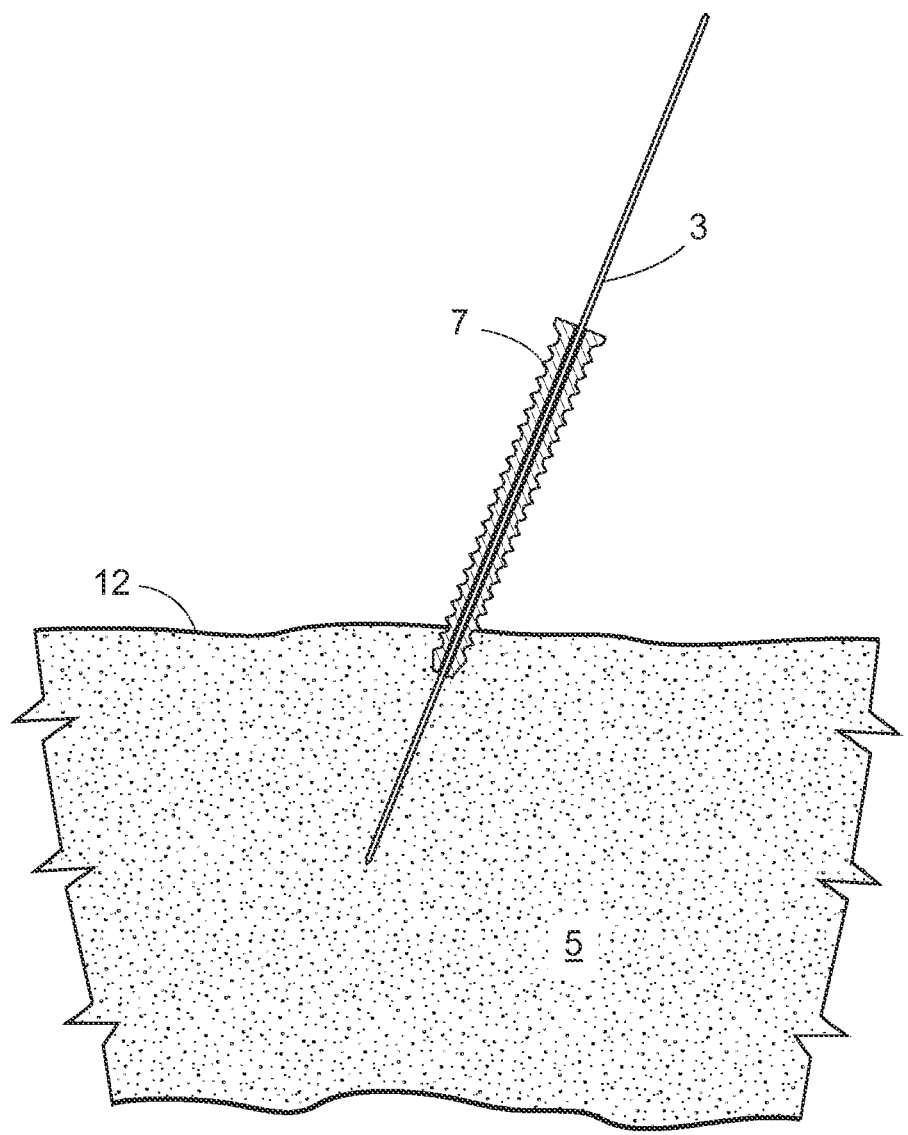
FIG. 6B illustrates the guide wire of FIG. 5 guiding a self-tapping cannulated screw into the bone shown in FIG. 5 in an embodiment.

Referring to FIG. 6A, when the screw 7 is sized, selected and/or determined based on the measured depth of the guide wire 3 or the drill bit 13, the thickness of the implant 9, the angle a of the hole 2 and/or the desired trajectory, the implant 9 having an opening 10 for a screw may be aligned with and/or lined up with the guide wire 3 inserted or positioned within the bone 5. Then the screw 7 may be placed, positioned and/or moved over guide wire 3 such that the guide wire 3 may pass through the shaft 8 until a distal tip 11 of the screw 7 touches, contacts or abuts an outer surface 12 of bone 5. Subsequently, the screw 7 may be screwed, twisted, turned and/or inserted into bone 5 as shown in FIG. 6A wherein the screw 7, or the distal tip 11 of the screw, has been partially screwed into bone 5. FIG. 6B illustrates the screw 7 partially screwed into bone 5 without the implant 9 being utilized. The implant 9 may be excluded if the screw 7 is being utilized to affix bone fragments and/or bones to each other.

It will be appreciated that several of the above-disclosed and other features and functions, or alternatives thereof, may be desirably combined into many other different guides and/or methods. Also, various presently unforeseen or unanticipated alternatives, modifications, variations or improvements therein may be subsequently made by those skilled in the art, and are also intended to be encompassed by the present disclosure.

We claim:

1. A drill or guide wire guide for use with at least one surgical implant screw, wherein the guide has a length defined between a first end and a second end located opposite to the first end and a thickness defined between a front side and a back side located opposite to the front side of the guide, wherein the guide comprises:
    a guide hole formed adjacent to the first end of the guide, wherein the guide hole extends through the thickness of the guide from the front side to the back side of the guide, wherein the guide hole has a diameter sized to receive a diameter of a drill bit or a guide wire; and
    a slot formed on the front side of the guide and located adjacent to the second end of the guide, wherein the slot extends along at least a portion of the length of the guide, wherein the slot is laterally accessible from the front side of the guide for the entire length of the slot, wherein the slot has a diameter sized to receive a diameter of a drill bit or a guide wire,
    wherein a longitudinal axis of the guide hole is angled from a longitudinal axis of the guide or the slot by an angle a, wherein the angle a is greater than about 1° and less than about 90°.

2. The guide according to claim 1, wherein the angle a is greater than about 30° and less than about 60°.

3. The guide according to claim 2, wherein the angle a is greater than about 45° and less than about 50°.

4. The guide according to claim 1, wherein an entire length of the slot is positioned between the guide hole and the second end of the guide.

5. The guide according to claim 1, further comprising:
    one or more sharp edges provided on at least one of the first end and second end of the guide, wherein the one or more sharp edges are configured to countersink a bone when the one or more sharp edges are positioned directly against the bone and rotated or moved.

6. The guide according to claim 5, wherein the one or more sharp edges comprise at least one of serrations and flutes.

7. The guide according to claim 6, wherein a cross-sectional shape of the one or more sharp edges is at least one of a circular shape and a semi-circular shape.

8. The guide according to claim 6, wherein the slot extends over more than about 30% of the length of the guide.

9. The guide according to claim 1, further comprising:
    a guide wire having a pre-determined length and a diameter less than the diameters of the guide hole and the slot such that the guide wire is insertable into the guide hole or the slot.

10. The guide according to claim 1, the guide further comprising:
    a measuring scale positioned adjacent to the slot for measuring an exposed portion of a length of a guide wire when the guide wire is positioned within the slot.

11. The guide according to claim 10, wherein at least a portion of the slot extends along an entire length of the measuring scale.

12. The guide according to claim 10, wherein the measuring scale ranges from at least about 5 mm to no more than about 250 mm.

13. A method of guiding a cannulated screw along a desired trajectory in a bone in orthopedic surgery, the method comprising:
    providing the guide according to claim 1 in an individual sterile package;
    inserting a guide wire into a bone at the desired trajectory via the guide hole of the guide;
    inserting the guide wire into a shaft of a surgical implant screw such that a first end of the screw is contactable with an outer surface of the bone; and
    inserting the screw into the bone along the desired trajectory provided by the guide hole of the guide.

14. The method according to claim 13, further comprising:
    removing the guide wire when the trajectory of the surgical implant screw has been established, wherein the surgical implant screw is a cannulated screw.

15. The method according to claim 13, further comprising:
    countersinking the bone by rotating or moving one or more sharp edges of the guide against the bone to remove a portion of the bone, wherein the one or more sharp edges are positioned on at least one of the first end and second end of the guide.

16. The method according to claim 15, wherein the one or more sharp edges comprise at least one of serrations and flutes, wherein, when the one or more sharp edges comprise at least flutes, the flutes are curved flutes.

17. A method of selecting a screw having a desired length, the method comprising:
    providing the guide according to claim 1;
    partially inserting a portion of a guide wire having a pre-determined length into a bone;
    measuring a portion of the guide wire that has not been inserted into the bone via the slot provided on the front side of the guide;
    determining a depth of the guide wire inserted into the bone based on the measured portion of the guide wire; and
    determining the desired length of the screw by adding the determined depth of the guide wire inserted into the bone and a distance that is traversable by the screw in a bone plate implant, when a bone plate implant is to be affixed to the bone.

18. The method according to claim 17, wherein the screw is a cannulated screw.

19. The method according to claim 17, wherein the portion of the guide wire that has not been inserted into the bone is inserted into the slot of the guide to determine the measured portion of the guide wire.

20. The method according to claim 19, wherein a measuring scale is located adjacent to the slot for determining the measured portion of the guide wire.

21. A drill or guide wire guide comprising:
- an elongate body having a first end, a second end, and a length inbetween the first and second ends aligned along a longitudinal axis;
- a lumen formed within the first end of the body, the lumen being aligned along an axis that is angled between about 1° and 90° with the longitudinal axis of the body;
- a planar surface on the body extending from the second end of the body for at least a portion of the length of the body; and
- a channel embedded in the planar surface extending from the second end of the body for at least a portion of the length of the body.

* * * * *